United States Patent [19]

Robinson et al.

[11] 4,181,688

[45] Jan. 1, 1980

[54] PHENOLIC RESOLS BLENDED WITH N-METHYLOL CARBAZOLES

[75] Inventors: Joseph G. Robinson, Winchcombe; Lesley D. Herbert, Stroud, both of England

[73] Assignee: Coal Industry (Patents) Limited, London, England

[21] Appl. No.: 962,164

[22] Filed: Nov. 20, 1978

[30] Foreign Application Priority Data

Nov. 25, 1977 [GB] United Kingdom ............... 49115/77

[51] Int. Cl.² .................. C08L 61/26; C08L 61/34
[52] U.S. Cl. ............................ 525/390; 260/32.8 N;
 428/460; 428/524; 428/531; 525/504; 528/163
[58] Field of Search ................ 260/839; 528/132, 163;
 428/524

[56] References Cited

U.S. PATENT DOCUMENTS

| | | | |
|---|---|---|---|
| 3,631,152 | 12/1971 | Johnson et al. | 528/163 X |
| 3,759,848 | 9/1973 | Omran et al. | 528/163 X |
| 3,829,528 | 8/1974 | Aarna et al. | 528/163 X |

OTHER PUBLICATIONS

Chem. Abstracts, vol. 64, 1966, 15823h, Lopatinskii et al.
Chem. Abstracts, vol. 76, 1972, 128019z, Omran et al.
Chem. Abstracts, vol. 79, 1973, 94518f, Omran et al.

*Primary Examiner*—Howard E. Schain
*Attorney, Agent, or Firm*—Stevens, Davis, Miller & Mosher

[57] ABSTRACT

Cross-linkable phenolic resols are known but do not have good water resistance. Phenolic resols can be blended with N-methylol carbazole or a derivative thereof to give a cross-linkable material useful for laminating or as a metal cement.

5 Claims, No Drawings

PHENOLIC RESOLS BLENDED WITH N-METHYLOL CARBAZOLES

This invention concerns phenolic resols, and more particularly concerns cross-linkable phenolic resol compositions.

Phenolic resols have been known for some time, and have been put to many uses. For instance, they have been used to form cotton and paper laminates but these have not particularly good resistance to water ingress.

It is an aim of the present invention to provide a phenolic resol which avoids to a large extent this problem. Initially, the possibility of combing the phenolic resol with carbazole was investigated. Using p-toluene sulphonic acid or sulphuric acid as catalyst, and 2-methoxyethanol or 50:50 industrial methylated spirits (IMS) and methyl isobutyl ketone (MIBK) as solvent, a certain amount of cross-linking was obtained on heating. That is, there was gel formation, but only a relatively small quantity (50–60%) of the reaction product was insoluble in acetone or in tetrahydrofuran.

It has now been surprisingly found that blends of a phenolic resol with N-methyl carbazole can be cross-linked to give substantial gel formation and products which are 95 to 100% insoluble in acetone (British Standard BS 2782).

The present invention provides a cross-linkable phenolic resol composition comprising 1 part by weight of an N-methylol carbazole and from 1.5 to 5, preferably 1.75 to 4, especially approximately 2 to 3, parts by weight of a phenolic resol.

The resol composition may be cross-linked by heating at a temperature of 120° to 150° C. or by adding an acid hardener such as hydrochloric acid or p-toluene sulphonic acid. If an acid is used, the composition may be heated to approximately 50° C. to accelerate the cross-linking.

The N-methylol carbazole may have alkyl or aryl substituents on its aromatic rings, such as methyl, ethyl or phenyl groups. Preferably, however, N-methylol carbazole itself is used.

Although a method for the preparation of N-methylol carbazole is described in Chemical Abstracts 64 (1966) 15823h, it was found that the product was substantially contaminated with carbazole (up to 30% free carbazole) and did not yield good cross-linked resins according to the present invention. The preparation of substantially pure N-Methylol carbazole is described in co-pending application Ser. No. 962,165 (British Application No. 54253/77). The preferred preparation is by the reaction of carbazole or a substituted derivative thereof with formalin in the presence of a basic catalyst such as calcium hydroxide, at a temperature of about 55° to 60° C. The reaction is preferably carried out in a solvent, such as IMS or ethanol.

The phenolic resol may be made by any conventional technique such as by the reaction of a phenol under reflux with formalin in the presence of a base, e.g. sodium hydroxide, in known manner. The product finally obtained is neutralised with an acid e.g. oxalic acid. Alternatively, ammonium hydroxide may be used as the basic catalyst, when the free resol is obtained without acidification. The phenol may be phenol itself or an alkylated phenol, such as a cresol or xylenol, or a dihydric phenol, such as catechol.

The composition according to the invention has the advantage that, when cross-linked, it is substantially or totally insoluble in common organic solvents such as acetone. The composition of the invention may also be used to advantage in rubber compounding, as an antioxidant. Another advantage of the compositions of the invention is that they may be used to make minimum odour grades of moulding powder.

Other uses of the compositions according to the invention will be apparent to those skilled in the art of phenolic resin technology.

The invention will now be illustrated by Example. Hereinafter, all parts and percentages are by weight unless otherwise indicated.

EXAMPLE

(i) Preparation of N-Methylol Carbazole (NMC)

105 parts of carbazole, 145 parts of formalin (40% W/V formaldehyde in water) and 265 parts of IMS were thoroughly mixed and then 10 parts of calcium hydroxide added. The mixture was heated with stirring at a temperature of 56° to 58° C. for an hour and thereafter filtered to remove unreacted carbazole and the calcium hydroxide. As the IMS cooled, the product N-methylol carbazole crystallised out of solution. The white crystals were separated by filtration and dried under vacuum at 50° C. for 2 hours. The crystals were identified by proton NMR and IR spectroscopy as NMC, m.p. 127°–129° C., and contained less than 1% carbazole according to gel permeation chromatography, which was used with a U.V. detector. ($\lambda = 254$ mm).

(ii) Preparation of Phenolic Resol (PR)

188 parts of phenol, 199.5 parts of formalin (see above) and 3.75 parts of sodium hydroxide were heated together under reflux for 45 minutes. The reaction temperature was between about 95° and 100° C. At the end of this time, the sodium hydroxide was neutralised by the addition of 8 parts of oxalic acid dissolved in 50 parts of water. The sodium oxalate was then filtered off and excess water distilled off, leaving a syrupy phenolic resol.

(iii) Preparation of Resol Compositions According to the Invention 2 parts PR and 1 part NMC were blended together to give Blend 1. Blend 2 similarly obtained from 3 parts PR and 1 part NMC.

Blend 1 was heated at 150° C. for 1 hour, to effect cross-linking, yielding a brittle solid mass. This was extracted with boiling acetone for 6 hours, whereupon less than 5% was extracted.

(iv) Preparation of Laminates (a) The Blends 1 and 2 were dissolved in methyl ethyl ketone (MEK) to give a varnish of approximately 50% solids contents. Ten 15×15 cm sheets of cotton cloth were dried in an oven at 90° C. for 1 hour, then weighed and impregnated with varnish. The impregnated sheets were air dried for 1 hour, then dried in an oven at 135° C. for 10 or 15 minutes (Pre-cure time). The sheets were then stacked one on top of the other and heated under 15 Kg/cm$^2$ pressure for 1 hour at 165° C.

The water absorbency of the laminates when measured according to the procedure of BS 2782:1970, method 502D, are shown below.

| Laminate No. | PR:NMC | Solids content of varnish (%) | Pre-cure temp. (°C.) | Pre-cure time (min.) | Cure temp (°C.) | Resin content of laminate (%) | Water abs. (%) |
| --- | --- | --- | --- | --- | --- | --- | --- |
| 1 | 3:1 | 50 | 135 | 15 | 165 | 39.0 | 2.2 |
| 2 | 2:1 | 50 | 135 | 15 | 165 | 44.7 | 1.7 |

The laminates were an orange-brown colour.

(b) 15 cm×15 cm sheets of Kraft Paper (130 μm Absorbent Kraft Paper, Cooke & Nuttal Ltd.) were air dried at 130° C. for 30 minutes, placed on a 61×61 cm glass plate and impregnated with varnish as described above, using a 3.8 cm diamter hand roller. The sheets were air dried for 30 min. and then suspended in an air oven at 130° C., to effect a pre-cure, for 15 minutes. A laminate was formed by stacking 8 pre-cured sheets between two 20×20 cm stainless steel plates covered with aluminium foil, and heating at 175° C. under a pressure of 15 Kg/cm² for 1 hour. To enable gases and water vapour to escape, the pressure was momentarily released 2 min. after its application. At the end of the cure time, the laminate was allowed to cool to room temperature while maintaining the pressure. It was then removed for evaluation. Rigid laminates of low water absorbency (1.6 to 2.8%) were obtained. The resin content of the laminate varied from 21.3% with only 5 min. pre-cure to 52.9% with 15 min. pre-cure.

(v) Preparation of Metal Cements

Blend 1 was pasted onto aluminium strips, to make lap joints (1.25×2.50 cm), which were then clamped together and heated at 135° C. Varying levels (0–10%) of a plasticiser such as polyvinyl acetate (PVA) were also added to the blend and evaluated. The shear strengths of the lap joints cured for various times are shown below:

| Sample No. | Cure Temp (°C.) | Cure Time (min) | PVA content (% w/w) | Force (kg) | Sheer Strength (kg/cm²) |
| --- | --- | --- | --- | --- | --- |
| 1A | 135 | 15 | — | 11 | 1.7 |
| 1B | 135 | 30 | — | ~ 60 | 9.2 |
| 1C | 135 | 45 | — | n.d. | n.d. |
| 1D | 135 | 60 | — | 36 | 5.6 |
| 2A | 135 | 15 | 5 | 3 | 0.5 |
| 2B | 135 | 30 | 5 | ~ 70 | 10.9 |
| 2C | 135 | 45 | 5 | 54 | 8.4 |
| 2D | 135 | 60 | 5 | ~ 60 | 9.3 |
| 3A | 135 | 15 | 10 | 6 | 0.9 |
| 3B | 135 | 30 | 10 | .33 | 5.1 |
| 3C | 135 | 45 | 10 | ~ 70 | > 11 |
| 3D | 135 | 60 | 10 | ~ 70 | > 11 |

(N.B. Forces > 55 kg are estimates).
(n.d. = not determined).

We claim:

1. A cross-linkable phenolic resol material comprising 1 part by weight of a N-methylol carbazole and from 1.5 to 5 parts by weight of a phenolic resol.

2. A cross-linkable material as claimed in claim 1, wherein the amount of phenolic resol is from 1.75 to 4 parts by weight.

3. A cross-linkable material as claimed in claim 2, wherein the amount of phenolic resol is from 2 to 3 parts by weight.

4. A cross-linkable material as claimed in claim 1, wherein N-methylol carbazole itself is used.

5. A water resistant laminate or metal-to-metal bond comprising a cross-linked material as claimed in claim 1.

* * * * *